(12) United States Patent
Pincus

(10) Patent No.: US 9,765,117 B2
(45) Date of Patent: Sep. 19, 2017

(54) PEPTIDES FOR TREATING CANCER

(71) Applicant: Romek Figa, Hanover, MA (US)

(72) Inventor: Matthew R. Pincus, Brooklyn, NY (US)

(73) Assignee: Romek Figa, Hanover, MA (US)

( * ) Notice: Subject to any disclaimer, the term of this patent is extended or adjusted under 35 U.S.C. 154(b) by 0 days.

(21) Appl. No.: 15/231,839

(22) Filed: Aug. 9, 2016

(65) Prior Publication Data

US 2017/0057999 A1 Mar. 2, 2017

Related U.S. Application Data

(60) Provisional application No. 62/209,182, filed on Aug. 24, 2015.

(51) Int. Cl.
| | |
|---|---|
| *A61K 38/00* | (2006.01) |
| *A61K 38/04* | (2006.01) |
| *C07K 14/00* | (2006.01) |
| *C07K 7/08* | (2006.01) |
| *C07K 14/47* | (2006.01) |

(52) U.S. Cl.
CPC .............. *C07K 7/08* (2013.01); *C07K 14/00* (2013.01); *C07K 14/4746* (2013.01); *A61K 38/00* (2013.01)

(58) Field of Classification Search
CPC ........ A61K 38/00; A61K 38/04; C07K 14/00; C07K 14/4746; C07K 7/08; C07K 2319/00
USPC .......................... 514/1.1, 21.4; 530/300, 326
See application file for complete search history.

(56) References Cited

U.S. PATENT DOCUMENTS

| | | | |
|---|---|---|---|
| 5,770,377 A | 6/1998 | Picksley et al. ............... 435/7.1 |
| 7,531,515 B2 | 5/2009 | Pincus ............................. 514/14 |
| 7,745,405 B2 | 6/2010 | Pincus ............................. 514/12 |
| 7,883,888 B2 | 2/2011 | Michl et al. ............... 435/320.1 |
| 8,822,419 B2 | 9/2014 | Pincus et al. ................ 514/19.2 |
| 2011/0183915 A1 | 7/2011 | Pincus et al. ................ 514/19.3 |
| 2014/0371156 A1 | 12/2014 | Pincus et al. ................ 514/18.9 |

OTHER PUBLICATIONS

Alarcon-Vargas, et al., "p53-MDM₂—The Affair that Never Ends," *Carcinogenesis*, vol. 23, No. 4, pp. 541-547 (2002).
Bowne, WB, et al., "The Penetratin Sequence in the Anticancer PNC-28 Peptide Causes Tumor Cell Necrosis Rather than Apoptosis of Human Pancreatic Cancer Cells," *Ann. Surg. Oncol.*, vol. 15, No. 12, pp. 3588-3600, Dec. 2008.
Dathe, M., et al., "Structural Features of Helical Antimicrobial Peptides: Their Potential to Modulate Activity on Model Membranes and Biological Cells," *Biochimica et Biophysica Acta (BBA) Biomembranes*, vol. 1462, Issues 1-2, pp. 71-87, Dec. 15, 1999.
Davitt, K, et al., "The Anti-Cancer Peptide, PNC-27, Induces Tumor Cell Necrosis of a Poorly Differentiated Non-Solid Tissue Human Leukemia Cell Line that Depends on Expression of HDM-2 in the Plasma Membrane of These Cells," *Ann. Clin. Lab Sci.*, vol. 44, No. 3, pp. 241-248 (2014).
Do, T., et al., "Preferential Induction of Necrosis in Human Breast Cancer Cells by a p53 peptide Dereived from the MDM₂ Binding Site," *Oncogene*, vol. 22, pp. 1431-1444 (2003).
Elmquist, A., et al., "VE-Cadherin-Derived Cell-Penetrating Peptide, pVEC, with Carrier Functions," *Exp. Cell. Res.*, vol. 269, Issue 2, pp. 237-244, Oct. 2001.
Futaki, S., et al., "Arginine-Rich Peptides—An Abundant Source of Membrane-Permeable Peptides Having Potential as Carriers for Intercellular Protein Delivery," *J. Biol. Chem.*, vol. 276, pp. 5836-5840, Feb. 2001.
Haffner, R., et al., "Biological Properties and Biological Effects of p53," *Current Opinion in Genetics & Development*, vol. 5, Issue 1, pp. 84-90, Feb. 1995.
Rosal, R., et al., "The Role of Alpha-Helical Structure in p53 Peptides as a Determinant for Their Mechanism of Cell Death: Necrosis Versus Apoptosis," *Advanced Drug Delivery Reviews*, vol. 57, Issue 4, pp. 653-660, Feb. 28, 2005.
Sarafraz-Yazdi, E., et al., "Anticancer Peptide PNC-27 Adopts an HDM-2-Binding Conformation and Kills Cancer Cells by Biding to HDM-2 in Their Membranes," *Proc. Natl. Acad. Sci. USA*, vol. 107, No. 5, pp. 1918-1923, Feb. 2, 2010.
Sarafraz-Yazdi, E., et al., "Ex vivo Efficacy of Anti-Cancer Drug PNC-27 in the Treatment of Patient-Derived Epithelial Ovarian Cancer," *Ann. Clin. Lab Sci.*, vol. 45, No. 6, pp. 650-658, Nov.-Dec. 2015.
Scheller, et al., "Evidence for an Amphipathicity Independent Cellular Uptake of Amphipathic Cell-Penetrating Peptides," *Eur. J. Biochem.*, vol. 267, pp. 6043-6049 (2000).
Tamilarasu, N., et al., "High Affinity and Specific Binding of HIV-1 TAR RNA by a Tat-Derived Oligourea," *J. Am. Chem. Soc.*, vol. 121, No. 7, pp. 1597-1598 (1999).
Tamilarasu, N., et al., "Targeting RNA with Peptidomimetic Oligomers in Human Cells," *Bioorg. Of Med. Chem. Lett.*, vol. 11, Issue 4, pp. 505-507, Feb. 26, 2001.

(Continued)

*Primary Examiner* — Julie Ha
(74) *Attorney, Agent, or Firm* — Sunstein Kann Murphy & Timbers LLP

(57) ABSTRACT

Provided are novel peptides having a human minute binding protein-2 (HDM-2) targeting sequence that target the human minute binding protein-2. Also provided are fusion proteins comprising an HDM-2 targeting sequence. Also provided are methods of using the peptides to treat cancer.

13 Claims, No Drawings

(56) References Cited

OTHER PUBLICATIONS

Wang, X. et al., "HIV-1 TAR RNA Recognition by an Unnatural Biopolymer," *J. Am. Chem. Soc.*, vol. 119, vol. 27, pp. 6444-6445 (1997).

Wasylyk, C., et al., "p53 Mediated Death of Cells Overexpressing $MDM_2$ by an Inhibitor of $MDM_2$Interaction with p53," *Oncogene*, vol. 18, pp. 1921-1934 (1999).

SEQUENCE LISTING

```
<160> NUMBER OF SEQ ID NOS: 41

<210> SEQ ID NO 1
<211> LENGTH: 15
<212> TYPE: PRT
<213> ORGANISM: Artificial
<220> FEATURE:
<223> OTHER INFORMATION: peptide

<400> SEQUENCE: 1

Pro Pro Leu Ser Gln Glu Thr Phe Ser Asp Leu Trp Lys Leu Leu
1               5                   10                  15

<210> SEQ ID NO 2
<211> LENGTH: 17
<212> TYPE: PRT
<213> ORGANISM: Artificial
<220> FEATURE:
<223> OTHER INFORMATION: peptide

<400> SEQUENCE: 2

Pro Pro Leu Ser Gln Thr Ser Phe Ala Glu Tyr Trp Asn Leu Leu Ser
1               5                   10                  15

Pro

<210> SEQ ID NO 3
<211> LENGTH: 34
<212> TYPE: PRT
<213> ORGANISM: Artificial
<220> FEATURE:
<223> OTHER INFORMATION: peptide

<400> SEQUENCE: 3

Pro Pro Leu Ser Gln Thr Ser Phe Ala Glu Tyr Trp Asn Leu Leu Ser
1               5                   10                  15

Pro Lys Lys Trp Lys Met Arg Arg Asn Gln Phe Trp Val Lys Val Gln
            20                  25                  30

Arg Gly

<210> SEQ ID NO 4
<211> LENGTH: 17
<212> TYPE: PRT
<213> ORGANISM: Artificial
<220> FEATURE:
<223> OTHER INFORMATION: peptide

<400> SEQUENCE: 4

Lys Lys Trp Lys Met Arg Arg Asn Gln Phe Trp Val Lys Val Gln Arg
1               5                   10                  15

Gly
```

```
<210> SEQ ID NO 5
<211> LENGTH: 14
<212> TYPE: PRT
<213> ORGANISM: Artificial
<220> FEATURE:
<223> OTHER INFORMATION: peptide

<400> SEQUENCE: 5

Tyr Gly Arg Lys Lys Arg Arg Gln Arg Arg Pro Pro Gln
1               5                   10

<210> SEQ ID NO 6
<211> LENGTH: 13
<212> TYPE: PRT
<213> ORGANISM: Artificial
<220> FEATURE:
<223> OTHER INFORMATION: peptide

<400> SEQUENCE: 6

Gly Arg Lys Lys Arg Arg Gln Arg Arg Pro Pro Gln
1               5                   10

<210> SEQ ID NO 7
<211> LENGTH: 13
<212> TYPE: PRT
<213> ORGANISM: Artificial
<220> FEATURE:
<223> OTHER INFORMATION: peptide

<400> SEQUENCE: 7

Gly Ala Ala Ala Ala Ala Ala Ala Ala Pro Pro Gln
1               5                   10

<210> SEQ ID NO 8
<211> LENGTH: 7
<212> TYPE: PRT
<213> ORGANISM: Artificial
<220> FEATURE:
<223> OTHER INFORMATION: peptide

<400> SEQUENCE: 8

Pro Lys Lys Lys Arg Lys Val
1               5

<210> SEQ ID NO 9
<211> LENGTH: 16
<212> TYPE: PRT
<213> ORGANISM: Artificial
<220> FEATURE:
<223> OTHER INFORMATION: peptide

<400> SEQUENCE: 9

Lys Arg Pro Ala Ala Ile Lys Lys Ala Gly Gln Ala Lys Lys Lys Lys
1               5                   10                  15

<210> SEQ ID NO 10
<211> LENGTH: 17
<212> TYPE: PRT
<213> ORGANISM: Artificial
<220> FEATURE:
<223> OTHER INFORMATION: peptide

<400> SEQUENCE: 10

Thr Arg Gln Ala Arg Arg Asn Arg Arg Arg Arg Trp Arg Glu Arg Gln
1               5                   10                  15

Arg
```

```
<210> SEQ ID NO 11
<211> LENGTH: 15
<212> TYPE: PRT
<213> ORGANISM: Artificial
<220> FEATURE:
<223> OTHER INFORMATION: peptide

<400> SEQUENCE: 11

Arg Arg Arg Arg Asn Arg Thr Arg Arg Asn Arg Arg Arg Val Arg
1               5                   10                  15

<210> SEQ ID NO 12
<211> LENGTH: 19
<212> TYPE: PRT
<213> ORGANISM: Artificial
<220> FEATURE:
<223> OTHER INFORMATION: peptide

<400> SEQUENCE: 12

Lys Met Thr Arg Ala Gln Arg Arg Ala Ala Ala Arg Arg Asn Arg Trp
1               5                   10                  15

Thr Ala Arg

<210> SEQ ID NO 13
<211> LENGTH: 13
<212> TYPE: PRT
<213> ORGANISM: Artificial
<220> FEATURE:
<223> OTHER INFORMATION: peptide

<400> SEQUENCE: 13

Thr Arg Arg Gln Arg Thr Arg Arg Ala Arg Arg Asn Arg
1               5                   10

<210> SEQ ID NO 14
<211> LENGTH: 19
<212> TYPE: PRT
<213> ORGANISM: Artificial
<220> FEATURE:
<223> OTHER INFORMATION: peptide

<400> SEQUENCE: 14

Lys Leu Thr Arg Ala Gln Arg Arg Ala Ala Arg Lys Asn Lys Arg
1               5                   10                  15

Asn Thr Arg

<210> SEQ ID NO 15
<211> LENGTH: 17
<212> TYPE: PRT
<213> ORGANISM: Artificial
<220> FEATURE:
<223> OTHER INFORMATION: peptide

<400> SEQUENCE: 15

Asn Ala Lys Thr Arg Arg His Glu Arg Arg Lys Leu Ala Ile Glu
1               5                   10                  15

Arg

<210> SEQ ID NO 16
<211> LENGTH: 22
<212> TYPE: PRT
<213> ORGANISM: Artificial
<220> FEATURE:
<223> OTHER INFORMATION: peptide
```

<400> SEQUENCE: 16

Met Asp Ala Gln Thr Arg Arg Glu Arg Ala Glu Lys Gln Ala
1               5                   10                  15

Gln Trp Lys Ala Ala Asn
            20

<210> SEQ ID NO 17
<211> LENGTH: 18
<212> TYPE: PRT
<213> ORGANISM: Artificial
<220> FEATURE:
<223> OTHER INFORMATION: peptide

<400> SEQUENCE: 17

Thr Ala Lys Thr Arg Tyr Lys Ala Arg Ala Glu Leu Ile Ala Glu
1               5                   10                  15

Arg Arg

<210> SEQ ID NO 18
<211> LENGTH: 16
<212> TYPE: PRT
<213> ORGANISM: Artificial
<220> FEATURE:
<223> OTHER INFORMATION: peptide

<400> SEQUENCE: 18

Thr Arg Arg Asn Lys Arg Asn Arg Ile Gln Glu Gln Leu Asn Arg Lys
1               5                   10                  15

<210> SEQ ID NO 19
<211> LENGTH: 12
<212> TYPE: PRT
<213> ORGANISM: Artificial
<220> FEATURE:
<223> OTHER INFORMATION: peptide

<400> SEQUENCE: 19

Ser Gln Met Thr Arg Gln Ala Arg Arg Leu Tyr Val
1               5                   10

<210> SEQ ID NO 20
<211> LENGTH: 26
<212> TYPE: PRT
<213> ORGANISM: Artificial
<220> FEATURE:
<223> OTHER INFORMATION: peptide

<400> SEQUENCE: 20

Lys Arg Arg Ile Arg Arg Glu Arg Asn Lys Met Ala Ala Ala Lys Ser
1               5                   10                  15

Arg Asn Arg Arg Arg Glu Leu Thr Asp Thr
            20                  25

<210> SEQ ID NO 21
<211> LENGTH: 28
<212> TYPE: PRT
<213> ORGANISM: Artificial
<220> FEATURE:
<223> OTHER INFORMATION: peptide

<400> SEQUENCE: 21

Arg Ile Lys Ala Glu Arg Lys Arg Met Arg Asn Arg Ile Ala Ala Ser
1               5                   10                  15

Lys Ser Arg Lys Arg Lys Leu Glu Arg Ile Ala Arg
            20                  25

<210> SEQ ID NO 22
<211> LENGTH: 22
<212> TYPE: PRT
<213> ORGANISM: Artificial
<220> FEATURE:
<223> OTHER INFORMATION: peptide

<400> SEQUENCE: 22

Lys Arg Ala Arg Asn Thr Glu Ala Ala Arg Arg Ser Arg Ala Arg Lys
1               5                   10                  15

Leu Gln Arg Met Lys Gln
            20

<210> SEQ ID NO 23
<211> LENGTH: 18
<212> TYPE: PRT
<213> ORGANISM: Artificial
<220> FEATURE:
<223> OTHER INFORMATION: peptide

<400> SEQUENCE: 23

Lys Leu Ala Leu Lys Leu Ala Leu Lys Ala Leu Lys Ala Ala Leu Lys
1               5                   10                  15

Leu Ala

<210> SEQ ID NO 24
<211> LENGTH: 18
<212> TYPE: PRT
<213> ORGANISM: Artificial
<220> FEATURE:
<223> OTHER INFORMATION: peptide

<400> SEQUENCE: 24

Leu Leu Ile Ile Leu Arg Arg Arg Ile Arg Lys Gln Ala Lys Ala His
1               5                   10                  15

Ser Lys

<210> SEQ ID NO 25
<211> LENGTH: 8
<212> TYPE: PRT
<213> ORGANISM: Artificial
<220> FEATURE:
<223> OTHER INFORMATION: peptide

<400> SEQUENCE: 25

Arg Arg Arg Arg Arg Arg Arg Arg
1               5

<210> SEQ ID NO 26
<211> LENGTH: 17
<212> TYPE: PRT
<213> ORGANISM: Artificial
<220> FEATURE:
<223> OTHER INFORMATION: peptide
<220> FEATURE:
<221> NAME/KEY: MISC_FEATURE
<222> LOCATION: (1)..(5)
<223> OTHER INFORMATION: Each amino acid in positions 1-5,
      independently, may be any amino acid, provided the fusion peptide
      causes death of cells which over-express HDM-2
<220> FEATURE:
<221> NAME/KEY: MISC_FEATURE
<222> LOCATION: (8)..(8)
<223> OTHER INFORMATION: Each amino acid in position 8, independently,

```
         may be any amino acid, provided the fusion peptide causes death
         of cells which over-express HDM-2

<400> SEQUENCE: 26

Xaa Xaa Xaa Xaa Xaa Thr Ser Xaa Ala Glu Tyr Trp Asn Leu Leu Ser
1               5                   10                  15

Pro

<210> SEQ ID NO 27
<211> LENGTH: 30
<212> TYPE: PRT
<213> ORGANISM: Artificial
<220> FEATURE:
<223> OTHER INFORMATION: peptide

<400> SEQUENCE: 27

Met Pro Phe Ser Thr Gly Lys Arg Ile Met Leu Gly Glu Lys Lys Trp
1               5                   10                  15

Lys Met Arg Arg Asn Gln Phe Trp Val Lys Val Gln Arg Gly
            20                  25                  30

<210> SEQ ID NO 28
<211> LENGTH: 10
<212> TYPE: DNA
<213> ORGANISM: Artificial
<220> FEATURE:
<223> OTHER INFORMATION: synthetic-kozak sequence

<400> SEQUENCE: 28
gccaccatgg                                                              10

<210> SEQ ID NO 29
<211> LENGTH: 38
<212> TYPE: DNA
<213> ORGANISM: Artificial
<220> FEATURE:
<223> OTHER INFORMATION: Primer

<400> SEQUENCE: 29
ctacagcgat cgccatggtg aggagcaggc aaatgtgc                               38

<210> SEQ ID NO 30
<211> LENGTH: 38
<212> TYPE: DNA
<213> ORGANISM: Artificial
<220> FEATURE:
<223> OTHER INFORMATION: Primer

<400> SEQUENCE: 30
acgagacgcg tgggaaata agttagcaca atcatttg                                38

<210> SEQ ID NO 31
<211> LENGTH: 38
<212> TYPE: DNA
<213> ORGANISM: Artificial
<220> FEATURE:
<223> OTHER INFORMATION: Primer

<400> SEQUENCE: 31
ctacagcgat cgccatggtg aggagcaggc aaatgtgc                               38

<210> SEQ ID NO 32
<211> LENGTH: 56
<212> TYPE: DNA
<213> ORGANISM: Artificial
```

<220> FEATURE:
<223> OTHER INFORMATION: Primer

<400> SEQUENCE: 32
gcgtacgcgt ttacataatt acacacttgg ggaaataagt tagcacaatc atttgg    56

<210> SEQ ID NO 33
<211> LENGTH: 38
<212> TYPE: DNA
<213> ORGANISM: Artificial
<220> FEATURE:
<223> OTHER INFORMATION: Primer

<400> SEQUENCE: 33
ctacagcgat cgccatctac aggaacttgg tagtagtc    38

<210> SEQ ID NO 34
<211> LENGTH: 56
<212> TYPE: DNA
<213> ORGANISM: Artificial
<220> FEATURE:
<223> OTHER INFORMATION: Primer

<400> SEQUENCE: 34
gcgtacgcgt ttacataatt acacacttgg ggaaataagt tagcacaatc atttgg    56

<210> SEQ ID NO 35
<211> LENGTH: 18
<212> TYPE: DNA
<213> ORGANISM: Artificial
<220> FEATURE:
<223> OTHER INFORMATION: Primer

<400> SEQUENCE: 35
ggactttcca aaatgtcg    18

<210> SEQ ID NO 36
<211> LENGTH: 20
<212> TYPE: DNA
<213> ORGANISM: Artificial
<220> FEATURE:
<223> OTHER INFORMATION: Primer

<400> SEQUENCE: 36
attaggacaa ggctggtggg    20

<210> SEQ ID NO 37
<211> LENGTH: 13
<212> TYPE: PRT
<213> ORGANISM: Artificial
<220> FEATURE:
<223> OTHER INFORMATION: Primer

<400> SEQUENCE: 37

Met Pro Phe Ser Thr Gly Lys Arg Ile Met Leu Gly Glu
1               5                   10

<210> SEQ ID NO 38
<211> LENGTH: 45
<212> TYPE: DNA
<213> ORGANISM: Artificial
<220> FEATURE:
<223> OTHER INFORMATION: primer

<400> SEQUENCE: 38 cccctctga gtcaggaaac attttcagac ctatggaaac tacct    45

```
<210> SEQ ID NO 39
<211> LENGTH: 51
<212> TYPE: DNA
<213> ORGANISM: Artificial
<220> FEATURE:
<223> OTHER INFORMATION: primer

<400> SEQUENCE: 39
ccccctctga gtcagacttc ttttgctgaa tattggaatc tactttctcc t            51

<210> SEQ ID NO 40
<211> LENGTH: 102
<212> TYPE: DNA
<213> ORGANISM: Artificial
<220> FEATURE:
<223> OTHER INFORMATION: primer

<400> SEQUENCE: 40
ccccctctga gtcagacttc ttttgctgaa tattggaatc tactttctcc taaaaaatgg   60
aaaatgcgcc gcaaccagtt ttgggtgaaa gtgcagcgcg gc                     102

<210> SEQ ID NO 41
<211> LENGTH: 51
<212> TYPE: DNA
<213> ORGANISM: Artificial
<220> FEATURE:
<223> OTHER INFORMATION: peptide

<400> SEQUENCE: 41
aaaaaatgga aaatgcgccg caaccagttt tgggtgaaag tgcagcgcgg c            51
```

PEPTIDES FOR TREATING CANCER

PRIORITY

This application claims priority to Provisional Application U.S. Ser. No. 62/209,182, filed Aug. 24, 2015, which is hereby incorporated by reference in its entirety.

BACKGROUND

The p53 protein is a cell cycle regulatory protein. It functions to inhibit the oncogenic effects of a number of oncogene proteins that induce mitosis by blocking transcription of proteins that induce mitosis and by inducing the transcription of proteins that block mitosis, and promote apoptosis. There is a correlation between the absence of the p53 protein and cell transformation and malignant disease. Haffner, R & Oren, M. (1995) Curr. Opin. Genet. Dev. 5: 84-90.

The p53 protein consists of 393 amino acids and binds to another important regulatory protein, the MDM-2 protein. HDM-2 (human double minute) and MDM-2 (mouse double minute) are p53 specific E3 ubiquitin protein ligases that suppresses the transcriptional activity of the tumor suppressor p53 and promote its degradation thereby limiting the tumor suppressor function of p53. HDM-2 and MDM-2 induce ubiquitination of p53 and target it for proteolysis in the proteasome (Alarcon-Vargas et al. 2002 Carcinogenesis 23: 541-547). Each of HDM-2 and MDM-2 have a p53 binding domain.

The MDM-gene that encodes the MDM-2 protein is a known oncogene. The MDM-2 protein forms a complex with the p53 protein, which results in the degradation of the p53 protein by a ubiquination pathway. The p53 protein binds to MDM-2 protein using an amino acid sequence that includes residues 12-29 of the p53 protein (Haffner, R & Oren, M. (1995) Curr. Opin. Genet. Dev. 5: 84-90).

Overexpression or amplification of MDM-2 (HDM-2) protein has been found in 40-60% of human malignancies, including 50% of human breast tumors. It has been suggested that the anti-tumor effect of the p53 protein might be enhanced by peptides capable of interfering with the binding of the MDM-2 protein to the p53 protein. A number of investigators have suggested that the MDM-2/p53 complex might be a target for rational drug design. See, e.g., Christine Wasylyk et al., "p53 Mediated Death of Cells Overexpressing MDM2 by an Inhibitor of MDM2 Interaction with p53", Oncogene, 18, 1921-34 (1999), and U.S. Pat. No. 5,770,377 to Picksley et al. Cancers that have been shown to have an increased level of membrane associated HDM-2 include TUC-3 pancreatic cells, MIA-PaCa-2 human pancreatic cancer cells, MCF-7 human breast cancer cells, A-2058 human melanoma cells (Sarafraz-Yazdi, E. et al. 2010 Proc Natl Acad Sci USA 107(5): 1918-1923), K562 leukemia cells (Davitt et al. 2014 Annals of Clinical and Laboratory Science 44(3): 241-248) and primary human ovarian cancers (Sarafraz-Yazdi et al. 2015, Annals of Clinical and Laboratory Science, in press).

U.S. Pat. No. 8,822,419, U.S. Pat. No. 7,531,515, U.S. Pat. No. 7,883,888, U.S. Pat. No. 7,745,405, US 2011/0183915 and US 2014/0371156 are incorporated by reference.

SUMMARY OF THE INVENTION

The invention relates to novel peptides that target the human minute binding protein-2 (HDM-2) comprising an HDM-2-targeting amino acid sequence, as well as fusion peptides comprising this sequence, and the use of a peptide according to the invention for treatment of cancer.

The invention relates to a peptide comprising the amino acid sequence PPLSQTSFAEYWNLLSP (SEQ ID NO: 2). Preferably, the peptide further comprises a membrane penetrating amino acid sequence, which peptide has increased cellular uptake, and which preferably forms the carboxy terminal sequence of said peptide. In preferred embodiments, the membrane penetrating sequence comprises the amino acid sequence: KKWKMRRNQFWVKVQRG (SEQ ID NO: 4).

The invention also relates to a peptide comprising the amino acid sequence: H-Pro-Pro-Leu-Ser-Gln-Thr-Ser-Phe-Ala-Glu-Tyr-Trp-Asn-Leu-Leu-Ser-Pro-Lys-Lys-Trp-Lys-Met-Arg-Arg-Asn-Gln-Phe-Trp-Val-Lys-Val-Gln-Arg-Gly-OH (SEQ ID NO: 3).

The invention also relates to a peptide having a length of 8 amino acids to 35 amino acids, comprising a sequence consisting of the amino acid sequence PPLSQTSFAEYWNLLSP (SEQ ID NO: 2). The invention also relates to an HDM-2-targeting peptide comprising the amino acid sequence: $X_1\ X_2\ X_3\ X_4\ X_5\ TSX_6AEYWNLLSP$ (SEQ ID NO 26) wherein $X_1$-$X_7$, independently, may be any amino acid, provided the fusion peptide causes death of cells which over-express HDM-2.

The invention also relates to a fusion peptide sequence comprising SEQ ID NO: 26 and another sequence comprising a cell penetrating peptide.

A fusion peptide according to the invention may also include one or more cytotoxic components, for example, a toxin, a drug, a radionuclide, an antibody or antibody fragment and combinations thereof.

In preferred embodiments, an alpha helix stabilizing amino acid residue may be included at either or both the amino or carboxyl terminal ends of the HDM-2 targeting peptide or of the HDM-2 targeting portion of a fusion peptide. Amino acids that stabilize the alpha helix include Leu and Glu, (particularly on the amino terminal end of the helix), and Met and Phe. Therefore, in a preferred embodiment the amino terminus of the HDM-2 targeting peptide or the HDM-2 targeting portion of a fusion peptide comprises Leu, Glu, Met or Phe. In another preferred embodiment, the carboxy terminus of the HDM-2 targeting peptide or the HDM-2 targeting portion of a fusion peptide comprises Leu, Glu, Met or Phe.

Preferably, the HDM-2 targeting peptide or portion of a fusion peptide includes an amino acid sequence substantially identical to PPLSQETFSDLWKLL (SEQ ID NO. 1), which includes residues 12-26 of human p53 protein, and differs from the naturally occurring p53 sequence as follows: E at position 6 is substituted with T, T at position 7 is substituted with S, S at position 9 is substituted with A, D at position 10 is substituted with E, L at position 11 is substituted with Y and K at position 13 is substituted with N, and including two additional amino acids, S and P, at the carboxy terminus.

A peptide according to the invention may be in the form of a composition comprising the peptide, and/or a pharmaceutical composition comprising the peptide, in combination with a pharmaceutically acceptable carrier, and/or in the form of a kit comprising the peptide and packaging materials.

The invention also pertains to a method of treating cancer in a subject, comprising administering to the subject a therapeutically effective amount of a composition comprising a peptide of the invention; a method of selectively necrosing cells, comprising providing a plurality of cells, including at least one cancer cells and at least one normal cell, administering to the cells a composition wherein the composition comprises the peptide, and wherein said composition results in membranolysis of said cancer cells, but does not affect said normal cells; and to a method of causing membranolysis in cancer cells, comprising administering to at least one cancer cell a composition comprising the peptide.

In one embodiment, of a method of selectively necrosing cells or a method of causing membranolysis, membranolysis indicates necrosis of at least one cancer cell. The method can also include a step of measuring in a cell medium contacted with the cells a level of LDH, whereby an increase in the level of LDH in the cell medium after administering the compound as compared to the level of LDH in the cell medium prior to administering the compound indicates necrosis of at least one cancer cell. The method can also comprise the step of microscopy of the cells whereby morphology in the cells treated with the compound that is identical to untreated cells indicates the absence of necrosis. The compound can be administered at a dosage between 20 µmol/ml and 160 µmol/ml.

The method of treating cancer may further comprise the step of observing in a medium of the cancer cells an early release of LDH, observing membranolysis of the cancer cells, observing a decrease from a number of pre-treatment cancer cells to a number of post treatment cancer cells; observing tumor cell eradication; repeating the administering step until a result is reached; observing necrosis in the cancer cells; and or observing a non-response in the normal cell, wherein the non-response indicates the normal cell is unaffected.

DETAILED DESCRIPTION OF THE INVENTION

As used herein, "peptide" means at least 5 amino acids. In one aspect, a peptide is 5-35 amino acids, for example, 5, 6, 7, 8, 9, 10, 15, 20, 25, 30 or 35 amino acids. In another embodiment, a peptide is 8-30 amino acids (for example, 8, 9, 10, 11, 12, 13, 14, 15, 16, 17, 18, 19, 20, 25 or 30 amino acids). In another embodiment, a peptide is 8-20 amino acids. A peptide of the invention comprises at least 5 amino acid residues of residues 12-26 of the human p53 protein.

A peptide according to the invention can include D-amino acids, non-peptide or pseudo-peptide linkages and peptidyl mimics. In addition, the peptide and peptide mimics can be modified, e.g. glycosylated or methylated. Synthetic mimics of targeting peptides are also included.

The peptides of the invention can be used for treating a sample comprising both healthy, normal cells and cancer cells, including cell lines, tissue samples, tumors, and/or a subject diagnosed with cancer and in need of treatment.

The present invention provides methods of treating cancer using a fusion peptide as set forth herein.

"Cancer" refers to a group of diseases involving abnormal cell growth including but not limited to solid tissue tumor and non-solid tissue tumor cancers, for example, astrocytoma, bladder cancer, brain cancer, breast cancer, cervical cancer, colorectal cancer, endometrial cancer, gastric cancer, lung cancer, melanoma, leukemia, lymphoma, ovarian cancer, pancreatic cancer, prostate cancer, renal carcinoma, sarcoma, thyroid cancer, glioblastoma, multiple myeloma, myelodysplastic syndrome, mesothelioma, acute myeloid leukemia, childhood leukemia, chronic myeloid leukemia, myelodysplastic syndrome, Hodgkin's lymphoma, and Polycythemia Vera.

A fusion peptide according to the invention comprises a portion which is a transmembrane penetrating sequence or membrane resident peptide (MRP). MRP is required for induction of necrosis by the inventive peptides. Expression of the p53 sequence in the absence of the MRP in cancer cells causes wild-type p53-dependent apoptosis, or programmed cell death and not tumor cell necrosis.

In one embodiment the MRP includes predominantly positively charged amino acid residues since a positively charged leader sequence may stabilize the alpha helix of a subject peptide. Examples of MRPs which may be useful to the HDM-2 targeting compounds of the present invention are described in Futaki, S. et al (2001) Arginine-Rich Peptides, J. Biol. Chem. 276, 5836-5840, and include but are not limited to the following MRPs in Table 1, below. The MRP may be, for example, the peptides identified as SEQ ID NOs: 4-25 in Table 1. For some of the MRPs, the numbering of the amino acid residues making up the MRP is indicated in parentheses.

TABLE 1

| SEQ ID NO: | SEQUENCE | NAME |
|---|---|---|
| SEQ ID NO: 3 | PPLSQTSFAEYWNLLSPKKWKMRRNQFWVKVQRG | SLH-1 |
| SEQ ID NO: 4 | KKWKMRRNQFWVKVQRG | Membrane resident peptide (MRP), reverseomer of Antennapedia |
| SEQ ID NO: 5 | YGRKKRRQRRRPPQ | HIV-1 TAT(47-60), membrane resident peptide |
| SEQ ID NO: 6 | GRKKRRQRRRPPQ | D-TAT, membrane resident peptide |
| SEQ ID NO: 7 | GAAAAAAAAAPPQ | R-TAT G(R)$_9$PPQ, membrane resident peptide |
| SEQ ID NO: 8 | PKKKRKV | SV40-NLS, membrane resident peptide |

TABLE 1-continued

| SEQ ID NO: | SEQUENCE | NAME |
|---|---|---|
| SEQ ID NO: 9 | KRPAAIKKAGQAKKKK | nucleoplasmin-NLS, membrane resident peptide |
| SEQ ID NO: 10 | TRQARRNRRRRWRERQR | HIV REV (34-50), membrane resident peptide |
| SEQ ID NO: 11 | RRRRNRTRRNRRRVR | FHV (35-49) coat, membrane resident peptide |
| SEQ ID NO: 12 | KMTRAQRRAAARRNRWTAR | BMV GAG (7-25), membrane resident peptide |
| SEQ ID NO: 13 | TRRQRTRRARRNR | HTLV-II REX 4-16, membrane resident peptide |
| SEQ ID NO: 14 | KLTRAQRRAAARKNKRNTR | CCMV GAG (7-25), membrane resident peptide |
| SEQ ID NO: 15 | NAKTRRHERRRKLAIER | P22 N (14-30), membrane resident peptide |
| SEQ ID NO: 16 | MDAQTRRRERRAEKQAQWKAAN | LAMBDA N(1-22), membrane resident peptide |
| SEQ ID NO: 17 | TAKTRYKARRAELIAERR | Phi N (12-29), membrane resident peptide |
| SEQ ID NO: 18 | TRRNKRNRIQEQLNRK | YEAST PRP6 (129-124), membrane resident peptide |
| SEQ ID NO: 19 | SQMTRQARRLYV | HUMAN U2AF, membrane resident peptide |
| SEQ ID NO: 20 | KRRIRRERNKMAAAKSRNRRRELTDT | HUMAN C-FOS (139-164), membrane resident peptide |
| SEQ ID NO: 21 | RIKAERKRMRNRIAASKSRKRKLERIAR | HUMAN C-JUN (252-279), membrane resident peptide |
| SEQ ID NO: 22 | KRARNTEAARRSRARKLQRMKQ | YEAST GCN4, membrane resident peptide |
| SEQ ID NO: 23 | KLALKLALKALKAALKLA | Example membrane resident peptide (MRP) |
| SEQ ID NO: 24 | LLIILRRRIRKQAKAHSK | p-vec, membrane resident peptide |
| SEQ ID NO: 25 | RRRRRRRR | (Arg)8 or any poly-R from $(R)_4$-$(R)_{16}$, membrane resident peptide |

Additional MRPs useful according to the invention are described e.g., in Scheller et al. (2000) Eur. J. Biochem. 267:6043-6049, and Elmquist et al., (2001) Exp. Cell Res. 269:237-244, the contents of which are incorporated herein by reference in its entirety.

The positively charged MRP may include the amino acid sequence: KKWKMRRNQFWVKVQRG (SEQ ID NO: 4), which is related to the reverseomer sequence of the antennapedia sequence. The MRP can be attached to the carboxyl terminal end of a peptide of the invention (e.g. peptide) or to the amino terminal end of a peptide of the invention.

The invention also provides for amino acid insertional derivatives of the invention that include amino and/or carboxyl terminal fusions as well as intra-sequence insertions of single or multiple amino acids. Insertional amino acid sequence variants are those in which one or more amino acid residues are introduced into a predetermined site in a subject peptide although random insertion is also possible with suitable screening of the resulting product. Deletional variants may be made by removing one or more amino acids from the sequence of a subject peptide. Substitutional amino acid variants are those in which at least one residue in the sequence has been removed and a different residue inserted in its place.

When the synthetic peptide is derivatised by amino acid substitution, the amino acids are generally replaced by other amino acids having like properties such as hydrophobicity, hydrophilicity, electronegativety, bulky side chains and the like. As used herein, the terms "derivative", "analogue", "fragment", "portion" and "like molecule" refer to a subject peptide having the amino acid sequence as set forth in SEQ ID NOs: 2 or 3, having an amino acid substitution, insertion, addition, or deletion, as long as said derivative, analogue, fragment, portion, or like molecule retains the ability to enter and selectively kill transformed or neoplastic cells.

In certain embodiments, the compounds and compositions of the present invention have a three dimensional shape or conformation in an alpha-helix-loop-alpha-helix. Interaction of the composition with the cancer cell membrane is facilitated by the alpha-helix-loop-helix conformation.

Also contemplated are peptides having a degree of rigidity than is greater than that of the synthetic peptide SLH-1. The alpha-helix-loop-alpha-helix, that results in an amphipathic structure, in which hydrophobic amino acid residues occupy one face of the molecule while polar residues occupy the opposite face of the molecule, is one possible conformation of the molecule. A number of membrane-active peptides, such as melittin and magainin, have these required structures that result in cell membrane lysis though not with the same specificity as SLH-1. Thus, if agents can be administered to a peptide-based composition to increase the rigidity, or if a non-peptide, called a peptidomimetic, rigid molecules of similar size, with a similar amphipathic structure, may be employed with the present invention, then the conformation will more immediately affect the cancer cells. Rosal R, Brandt-Rauf P W, Pincus M R, Wang H, Mao Y, Fine R L. The role of alpha-helical structure in p53 peptides as a determinant for their mechanism of cell death: necrosis versus apoptosis. Adv Drug Deliv Rev 2005; 57:653-60; Pincus, M. R. (2001) "The Physiological Structure and Function of Proteins" in Principles of Cell Physiology (Chapter 2), Third Edition, Ed., N. Sperelakis, Academic Press, New York, pp. 19-42; 3. Dathe, M. and Wieprecht, T. (1999) Structural Features of Helical Anti-Microbial Peptides: Their Potential to Modulate Activity on Model Membranes and Biological Cells. Biochem. Biochem. Biophys. Acta 1462, 71-87.

In certain embodiments, the peptide of the invention is relatively small. It is more likely that large peptide, non-peptide, and combination peptide/non-peptide compositions will cause a significant immunologic response. Thus, the immune system of the subject being treated is less likely to trigger an immune response against small molecules, i.e. peptides of <35AA than large molecule compositions, i.e., proteins with >35AA. Preferably, the synthetic peptide materials of the present invention are on the order of about thirty-five (35) amino acids or fewer, for example, 35, 30, 25, 20, 19, 18, 17, 16, 15, 14, 13, 12, 11, 10, 9 or 8.

In another embodiment, the composition of the invention has a long half-life and remains in the body for longer periods of time before decomposing. A composition with a longer half-life may have an increased longevity, allowing it to be transported through the body to kill more cancer cells or treat cancers located in different parts of the organism upon a single administration. The invention provides for peptides, including SLH-1, modified to include a D-amino acid on the amino terminal end in order to slow peptidase activity of the molecule. In another embodiment, the peptidase inhibitor leupeptin may be attached to the carboxyl terminal end of SLH-1 to slow peptidase activity and lengthen the half-life of the molecules.

One or more of the methods referenced herein may optionally include a reiteration or repeated administration step. That is, after the administration step, it is possible to determine whether a plurality of subsequent cancer cells exist and remain intact. If so, it is possible to complete one or more of the method steps for each of the methods previously discussed, including the administration of the compound, HDM-2 recognition agent, and the like.

The compounds, agents, and materials used in conjunction with one or more of the aforementioned methods are desirably in a purified form. Purified form, as used herein, generally refers to material which has been isolated under certain desirable conditions that reduce or eliminate unrelated materials, i.e. contaminants. Substantially free from contaminants generally refers to free from contaminants within analytical testing and administration of the material. Preferably, purified material is substantially free of contaminants that is at least 50% pure, more preferably, at least 90% pure, and more preferably still at least 99% pure. Purity can be evaluated by conventional means, e.g. chromatography, gel electrophoresis, immunoassay, composition analysis, biological assay, NMR, and other methods known in the art.

At least one cancer cell, as used herein, may similarly refer to a plurality of cancer cells. A plurality of cells may include, a sample of cells, a tissue sample, a tumor, and/or even a subject having cancer. At least one cell may refer to one cell, a plurality of cells, a sample of cells, a tissue sample, and/or even a subject. A plurality of cells including at least one cancer cell and at least one non-cancerous cell may refer to a mixture of cells in a sample, an area of tissue including both cancerous and non-cancerous tissues, and or a subject diagnosed with cancer.

The term "subject", as used herein may refer to a patient or patient population diagnosed with, or at risk of developing one or more forms of cancer. Also, as used herein, a subject may refer to a living animal, including mammals, in which cancer may be induced through transplantation or xenotransplanting which may be subsequently treated with the methods and compounds of the present invention or which have developed cancer and need veterinary treatment. Such subjects may include mammals, for example, laboratory animals, such as mice, rats, and other rodents; monkeys, baboons, and other primates, etc. They may also include household pets or other animals in need of treatments for cancer.

The terms "therapeutically effective dosage" and "effective amount" refer to an amount sufficient to kill one or more cancer cells. A therapeutic response may be any response that a user (e.g. a clinician will recognize) exhibits as an effective response to the therapy, including the foregoing symptoms and surrogate clinical markers. Thus, a therapeutic response will generally be an amelioration or inhibition of one or more symptoms of a disease or disorder, e.g. cancer.

Administering, as referred to by one or more of the methods of the present invention, may include contacting. The term "contacting" refers to directly or indirectly bringing the cell and the compound together in physical proximity. The contacting may be performed in vitro or in vivo. For example, the cell may be contacted with the compound by delivering the compound into the cell through known techniques, such as microinjection into the tumor directly, injecting the compound into the bloodstream of a mammal, and incubating the cell in a medium that includes the compound.

Any method known to those in the art for contacting a cell, organ or tissue with a compound may be employed. Suitable methods include in vitro, ex vivo, or in vivo methods. In vitro methods typically include cultured samples. For example, a cell can be placed in a reservoir (e.g., tissue culture dish), and incubated with a compound under appropriate conditions suitable for inducing necrosis in cancer cells. Suitable incubation conditions can be readily determined by those skilled in the art.

Ex vivo methods typically include cells, organs or tissues removed from a mammal, such as a human. The cells, organs or tissues can, for example, be incubated with the compound under appropriate conditions. The contacted cells, organs or tissues are normally returned to the donor, placed in a recipient, or stored for future use. Thus, the compound is generally in a pharmaceutically acceptable carrier.

In vivo methods are typically limited to the administration of a compound, such as those described above, to a mammal, preferably a human. The compounds useful in the methods of the present invention are administered to a mammal in an amount effective in necrosing cancer cells for treating cancer in a mammal. The effective amount is determined during pre-clinical trials and clinical trials by methods familiar to physicians and clinicians.

The compounds useful in the methods of the invention may also be administered to mammals by sustained release, as is known in the art. Sustained release administration is a method of drug delivery to achieve a certain level of the drug over a particular period of time. The level typically is measured by serum or plasma concentration.

The compounds of one or more of the aforementioned methods of the present invention may be administered to a human in an amount effective in achieving its purpose. The effective amount of the compound to be administered can be readily determined by those skilled in the art, for example, during pre-clinical trials and clinical trials, by methods familiar to physicians and clinicians. Typical daily doses include approximately 1 mg to 1000 mg.

An effective amount of a compound useful in the methods of the present invention, preferably in a pharmaceutical composition, may be administered to a mammal in need thereof by any of a number of well-known methods for administering pharmaceutical compounds. The compound may be administered systemically or locally.

Any formulation known in the art of pharmacy is suitable for administration of the compounds useful in the methods of the present invention. For oral administration, liquid or solid formulations may be used. Some examples of formulations include tablets, capsules, such as gelatin capsules, pills, troches, elixirs, suspensions, syrups, wafers, chewing gum and the like. The compounds can be mixed with a suitable pharmaceutical carrier (vehicle) or excipient as understood by practitioners in the art. Examples of carriers and excipients include starch, milk, sugar, certain types of clay, gelatin, lactic acid, stearic acid or salts thereof, including magnesium or calcium stearate, talc, vegetable fats or oils, gums and glycols.

Formulations of the compounds useful in the methods of the present inventions may utilize conventional diluents, carriers, or excipients etc., such as those known in the art to deliver the compounds. For example, the formulations may comprise one or more of the following: a stabilizer, a surfactant, preferably a nonionic surfactant, and optionally a salt and/or a buffering agent. The compound may be delivered in the form of an aqueous solution, or in a lyophilized form. Similarly, salts or buffering agents may be used with the compound.

The compounds of the present invention may be administered in therapeutically effective concentrations, to be provided to a subject in standard formulations, and may include any pharmaceutically acceptable additives, such as excipients, lubricants, diluents, flavorants, colorants, buffers, and disintegrants. Standard formulations are well known in the art. See, e.g. Remington's pharmaceutical Sciences, 20th edition, Mach Publishing Company, 2000. The formulation may be produced in useful dosage units for administration by any route that will permit the compound to contact the cancer cell membranes. Exemplary routes of administration include oral, parenteral, transmucosal, intranasal, insulfation, or transdermal routes. Parenteral routes include intravenous, intra-arterial, intramuscular, intradermal, subcutaneous, intraperitoneal, intraductal, intraventricular, intrathecal, and intracranial administrations.

The pharmaceutical forms suitable for injection include sterile aqueous solutions or dispersions and sterile powders for the extemporaneous preparation of sterile injectable solutions or dispersions. The ultimate solution form in all cases must be sterile and fluid. Typical carriers include a solvent or dispersion medium containing, e.g., water buffered aqueous solutions, i.e., biocompatible buffers, ethanol, polyols such as glycerol, propylene glycol, polyethylene glycol, suitable mixtures thereof, surfactants or vegetable oils. Sterilization may be accomplished utilizing any art-recognized technique, including but not limited to filtration or addition of antibacterial or antifungal agents.

The compounds of the present invention may be administered as a solid or liquid oral dosage form, e.g. tablet, capsule, or liquid preparation. The compounds may also be administered by injection, as a bolus injection or as a continuous infusion. The compounds may also be administered as a depot preparation, as by implantation or by intramuscular injection.

The compounds, agents, and materials referenced in the present invention may be in a "pharmaceutically acceptable carrier". A pharmaceutically acceptable carrier includes any and all solvents, dispersion media, coatings, antibacterial and antifungal agents, isotonic agents and the like. The use of such media and agents are well-known in the art. The phase 'pharmaceutically acceptable' refers to molecular entities and compositions that are physiologically tolerable and do not typically produce unwanted reactions when administered to a subject, particularly humans. Preferably, as used herein, the term "pharmaceutically acceptable" means approved by a regulatory agency of the federal or a state government or listed in the U.S. Pharmacopeia or other generally recognized pharmacopeia for use in animals, and more particularly, in humans. The term carrier refers to a diluent, adjuvant, excipient or vehicle with which the compounds may be administered to facilitate delivery. Such pharmaceutical carriers can be sterile liquids, such as water and oils, or organic compounds. Water or aqueous saline solutions, and aqueous dextrose and glycerol solutions are preferably employed as carriers, particularly as injectable solutions.

The synthetic peptides which may include the compounds, agents, and materials used with the present methods of the present invention may be synthesized by a number of known techniques. For example, the peptides may be prepared using the solid-phase technique initially described by Merrifield (1963) in J. Am. Chem. Soc. 85:2149-2154. Other peptide synthesis techniques may be found in M. Bodanszky et al. Peptide Synthesis, John Wiley and Sons, 2d Ed., (1976) and other references readily available to those skilled in the art. A summary of polypeptide synthesis techniques may be found in J. Stuart and J. S. Young, Solid Phase Peptide Synthesis, Pierce Chemical Company, Rockford, Ill., (1984). Peptides may also be synthesized by solid phase or solution methods as described in The Proteins, Vol. II, 3d Ed., Neurath, H. et al., Eds., pp. 105-237, Academic Press, New York, N.Y. (1976). Appropriate protective groups for use in different peptide syntheses are described in the texts listed above as well as in J. F. W. McOmie, Protective Groups in Organic Chemistry, Plenum Press, New York, N.Y. (1973). The peptides of the present invention may also be prepared by chemical or enzymatic cleavage from larger portions of the p53 protein or from the full length p53 protein. Likewise, membrane-resident sequences for use in the synthetic peptides of the present invention may be prepared by chemical or enzymatic cleavage from larger portions or the full length proteins from which such leader sequences are derived.

Additionally, the peptides of the present invention may also be prepared by recombinant DNA techniques. For most amino acids used to build proteins, more than one coding nucleotide triplet (codon) can code for a particular amino acid residue. This property of the genetic code is known as redundancy. Therefore, a number of different nucleotide sequences may code for a particular subject peptide selectively lethal to malignant and transformed mammalian cells. The present invention also contemplates a deoxyribonucleic acid (DNA) molecule that defines a gene coding for, i.e., capable of expressing a subject peptide or a chimeric peptide from which a peptide of the present invention may be enzymatically or chemically cleaved.

The synthetic peptides of the present invention may be synthesized by a number of known techniques. For example, the peptides may be prepared using the solid-phase technique initially described by Merrifield (1963) in J. Am. Chem. Soc. 85:2149-2154. Other peptide synthesis techniques may be found in M. Bodanszky et al. Peptide Synthesis, John Wiley and Sons, 2d Ed., (1976) and other references readily available to those skilled in the art. A summary of polypeptide synthesis techniques may be found in J. Sturart and J. S. Young, Solid Phase Peptide Synthesis, Pierce Chemical Company, Rockford, Ill., (1984). Peptides may also be synthesized by solution methods as described in The Proteins, Vol. II, 3d Ed., Neurath, H. et al., Eds., pp. 105-237, Academic Press, New York, N.Y. (1976). Appropriate protective groups for use in different peptide syntheses are described in the texts listed above as well as in J. F. W. McOmie, Protective Groups in Organic Chemistry, Plenum Press, New York, N.Y. (1973). The peptides of the present invention may also be prepared by chemical or enzymatic cleavage from larger portions of the p53 protein or from the full length p53 protein. Likewise, leader sequences for use in the synthetic peptides of the present invention may be prepared by chemical or enzymatic cleavage from larger portions or the full length proteins from which such leader sequences are derived.

Additionally, the peptides of the present invention may also be prepared by recombinant DNA techniques. For most amino acids used to build proteins, more than one coding nucleotide triplet (codon) can code for a particular amino acid residue. This property of the genetic code is known as redundancy. Therefore, a number of different nucleotide sequences may code for a particular subject peptide selectively lethal to malignant and transformed mammalian cells. The present invention also contemplates a deoxyribonucleic acid (DNA) molecule that defines a gene coding for, i.e., capable of expressing a subject peptide or a chimeric peptide from which a peptide of the present invention may be enzymatically or chemically cleaved.

A peptide of the invention includes a peptide that is a substantially similar variant of SEQ ID Nos 1, 2, 3 and/or 4. A peptide of the invention includes a peptide that is a substantially similar variant of amino acid residues of the HDM-2 binding region of p53. A peptide of the invention includes a peptide that is a substantially similar variant of amino acid residues 12-26 of the p53 protein and include the amino acid sequence NLLSP.

A "substantially similar variant" may be at least 25% identical to a peptide of the invention, as long as it is able to target HDM-2 on the surface of cells, and/or provided it causes cell death. Of course, the percent identity can be higher, e.g., 30%, 35, 40%, 45%, 50%, 55%, 60%, 65%, 67%, 69%, 70%, 73%, 75%, 77%, 83%, 85%, 87%, 90%, 91%, 92%, 93%, 94%, 95%, 96%, 97%, 98%, or 99% identity. In general, the substitutions are conservative substitutions.

The variants thereof can also have substitutions, deletions or additions. Alterations may produce conservative or non-conservative amino acid substitutions, deletions or additions. In some embodiments the substitution, deletion or insertion is of 1, 2, 3, 4, 5, 6, 7, 8, 9 or more amino acids. The skilled artisan is fully aware of amino acid substitutions that are either less likely or not likely to significantly affect protein function (e.g., replacing one aliphatic amino acid with a second aliphatic amino acid). Guidance concerning how to make phenotypically silent amino acid substitutions is provided in Bowie, J. U. et al., "Deciphering the Message in Protein Sequences: Tolerance to Amino Acid Substitutions," Science 247:1306-1310 (1990).

The peptides or the variants thereof can also have modified backbones, e.g., oligocarbamate or oligourea backbones (see, e.g., Wang et al., J. Am. Chem. Soc. 119:6444-6445 (1997); Tamilarasu et al., J. Am. Chem. Soc. 121:1597-1598 (1999); Tamilarasu et al., Bioorg. Of Med. Chem. Lett. 11:505-507 (2001)).

Sequence identity may be determined by sequence comparison and alignment algorithms known in the art. To determine the percent identity of two amino acid sequences, the sequences are aligned for optimal comparison purposes (e.g., gaps can be introduced in the first sequence or second sequence for optimal alignment). The amino acid residues at corresponding amino acid positions are then compared. When a position in the first sequence is occupied by the same residue as the corresponding position in the second sequence, then the molecules are identical at that position. The percent identity between the two sequences is a function of the number of identical positions shared by the sequences (i.e., % homology=# of identical positions/total # of positions times 100), optionally penalizing the score for the number of gaps introduced and/or length of gaps introduced.

The comparison of sequences and determination of percent identity between two sequences can be accomplished using a mathematical algorithm. In one embodiment, the alignment generated over a certain portion of the sequence aligned having sufficient identity but not over portions having low degree of identity (i.e., a local alignment). A preferred, non-limiting example of a local alignment algorithm utilized for the comparison of sequences is the algorithm of Karlin and Altschul (1990) Proc. Natl. Acad. Sci. USA 87:2264-68, modified as in Karlin and Altschul (1993) Proc. Natl. Acad. Sci. USA 90:5873-77. Such an algorithm is incorporated into the BLAST programs (version 2.0) of Altschul, et al. (1990) J. Mol. Biol. 215:403-10.

In another embodiment, the alignment is optimized by introducing appropriate gaps and percent identity is determined over the length of the aligned sequences (i.e., a gapped alignment). To obtain gapped alignments for comparison purposes, Gapped BLAST can be utilized as described in Altschul et al., (1997) Nucleic Acids Res. 25(17):3389-3402. In another embodiment, the alignment is optimized by introducing appropriate gaps and percent identity is determined over the entire length of the sequences aligned (i.e., a global alignment). A preferred, non-limiting example of a mathematical algorithm utilized for the global comparison of sequences is the algorithm of Myers and Miller, CABIOS (1989). Such an algorithm is incorporated into the ALIGN program (version 2.0) which is part of the GCG sequence alignment software package. When utilizing the ALIGN program for comparing amino acid sequences, a PAM120 weight residue table, a gap length penalty of 12, and a gap penalty of 4 can be used.

Also provided are nucleic acid sequences encoding each of SEQ ID NOs: 1-4.

The nucleic acid sequence corresponding to SEQ ID NO: 1 is: ccc cct ctg agt cag gaa aca ttt tca gac cta tgg aaa cta cct (SEQ ID NO: 38).

The nucleic acid sequence corresponding to any one of SEQ ID NOs: 2-4 includes a sequence wherein each of the amino acids of SEQ ID NO: 2-4 is encoded by any of the corresponding DNA codons presented in Table 2.

TABLE 2

| Amino Acid | SLC | DNA codons |
|---|---|---|
| Isoleucine | I | ATT, ATC ATA |
| Leucine | L | CTT, CTC, CTA, CTG, TTA, TTG |
| Valine | V | GTT, GTC, GTA, GTG |
| Phenylalanine | F | TTT, TTC |
| Methionine | M | ATG |
| Cysteine | C | TGT, TGC |
| Alanine | A | GCT, GCC, GCA, GCG |
| Glycine | G | GGT, GGC GGA, GGG |
| Proline | P | CCT, CCC, CCA, CCG |
| Threonine | T | ACT, ACC, ACA, ACG |
| Serine | S | TCT, TCC, TCA, TCG, AGT, AGC |
| Tyrosine | Y | TAT, TAC |
| Tryptophan | W | TGG |
| Glutamine | Q | CAA, CAG |
| Asparagine | N | AAT, AAC |
| Histidine | H | CAT, CAC |
| Glutamic acid | E | GAA, GAG |
| Aspartic acid | D | GAT, GAC |
| Lysine | K | AAA, AAG |
| Arginine | R | CGT, CGC, CGA, CGG, AGA, AGG |
| Stop codons | Stop | TAA, TAG, TGA |

A representative nucleic acid sequence corresponding to SEQ ID NO: 2 is: ccc cct ctg agt cag act tct ttt gct gaa tat tgg aat cta ctt tct cct (SEQ ID NO: 39)

A representative nucleic acid sequence corresponding to SEQ ID NO: 3 is:
ccc cct ctg agt cag act tct ttt gct gaa tat tgg aat cta ctt tct cct aaa aaa tgg aaa atg cgc cgc aac cag ttt tgg gtg aaa gtg cag cgc ggc (SEQ ID NO: 40).

A representative nucleic acid sequence encoding SEQ ID NO: 4 is:
aaa aaa tgg aaa atg cgc cgc aac cag ttt tgg gtg aaa gtg cag cgc ggc (SEQ ID NO: 41).

Variations of each of SEQ ID NOs: 2-4 can occur due to redundancies in the genetic code.

Peptides

SLH-1, H-Pro-Pro-Leu-Ser-Gln-Thr-Ser-Phe-Ala-Glu-Tyr-Trp-Asn-Leu-Leu-Ser-Pro-Lys-Lys-Trp-Lys Met Arg Arg Asn-Gln-Phe-Trp-Val-Lys-Val-Gln-Arg-Gly-OH (SEQ ID NO: 2) (1 g), are synthesized using solid phase methods (Shaanxi Zhongbang Pharma-Tech Corp., Nanguan-Zhengjie, Xi'an, China) and was >95% pure by HPLC and mass spectrographic analysis. The italicized sequence corresponds to the MRP segment that allows entry of the whole peptide into cells. A negative control peptide, PNC-29, containing the X13 peptide from cytochrome P450 (bold) attached to the MRP (italics), H-Met-Pro-Phe-Ser-Thr-Gly-Lys-Arg-Ile-Met-Leu-Gly-Glu-Lys-Lys-Trp-Lys-Met-Arg-Arg-Asn-Gln-Phe-Trp-Val-Lys-Val-Gln-Arg-Gly-OH (SEQ ID NO: 27), is likewise synthesized by solid phase methods and is likewise >95% pure. The X13 peptide replaces the p53 sequence of SLH-1.

FITC- and TAMRA-Double Fluorophore-Labeled SLH-1 Peptide

This peptide is synthesized at the Biopeptide Corp., La Jolla, Calif., with two fluorescent labels: amino terminal 5,6-carboxy-fluorescein (green fluorescence) and carboxyl terminal 5-tetramethyl Rhodamine (TAMRA) (red fluorescence) and assessed for purity.

Plasmids

DNA encoding the modified human p53 amino acid sequence of SLH-1, is cloned into the mammalian pTracer-SV40 (green-fluorescent protein [GFP]-expressing) expression vector downstream to the SV40 promoter. This vector constitutively expresses a cloned gene (Invitrogen, Carlsbad, Calif.). Also included in the vector is another expression cassette which is linked in tandem to the SV40-p53 amino acid-expressing unit. The second expression cassette contains a CMV promoter driving the expression of the GFP-Zeocin resistance gene fusion protein. The vector is used to transform TOP10F' chemically competent *E. coli* using methods of transformation known in the art, and plated on Zeocin-containing agar plates for overnight growth. Eight colonies are then used to inoculate cultures in Low Salt Luria Broth (1% bacterial tryptone, 0.5% yeast extract, 0.5% NaCl, and 25 m/ml Zeocin). Cultures are grown under constant shaking at 200 rpm for 16 h in a 37° C. incubator and plasmids are extracted using a Qiagen Spin Miniprep Kit.

Construct sense and anti-sense strands of the cDNA encoding the p53 sequence of SLH-1 are synthesized. For maximum protein translation in transfected cell lines, the start codon is placed within a Kozak sequence, i.e., GCCACCATGG (SEQ ID NO: 28) (with ATG being the start codon), which is the optimal context for initiation of translation in vertebrate mRNA. The strands (250 nmol/ml) are annealed in annealing buffer by heating to 95° C., and then cooling to room temperature. The annealed double stranded sequence-encoding cDNA corresponding to the p53 sequence of SLH-1 is then digested with NotI and EcoRI simultaneously. For example, a total of 20 µg of pTracer-SV40 is digested with 60 units of NotI and 60 units of EcoRI. Double-digested pTracer-SV40 and cDNA encoding the p53 sequence of SLH-1 are then electrophoresed through 0.8% and 2.5% agarose gel, respectively. Gel bands containing DNA of appropriate size are excised, and DNA content is extracted using the NucleoTrap Gel Extraction kit (ClonTech, Mountain View, Calif.). Purified vector and cDNA are ligated with T4 ligase (for 12 hr, at 4° C.) (New England Biolab, Ipswich, Mass.). Two µl of ligation reaction is then dispensed into a vial containing 50 µl One Shot TOP10F' competent *E. coli* (Invitrogen), and the reaction mixture is incubated on ice for 10 min, heat-shocked to 42°

C. (30 sec) and incubated on ice for another 2 min. A total of 250 µl SOC medium (Invitrogen) is then added to the cells which are then shaken at 37° C. (1 hr). This transformation reaction is then diluted 1:100 or 1:10 using SOC medium. A total of 50 µl of each is spread on LB plates containing 12.5 µmol/ml ampicillin that are incubated overnight at 37° C. A representative number of colonies are randomly chosen to inoculate a corresponding number of 5 ml overnight LB cultures in the presence of 12.5 µmol/ml ampicillin. Plasmids extracted from each liquid culture are analyzed by automated DNA sequencing using the fluorescence-based dideoxy chain termination reaction (Genewiz, North Brunswick, N.J.) to determine if they contain the correct p53 cDNA reading frame associated with a stop codon and a start codon embedded in the Kozak sequence.

The same procedure is followed for preparation of a plasmid encoding a scrambled sequence comprising the amino acids of the p53 peptide sequence of SLH-1, with start, stop codons, and restriction enzyme sites denoted as above.

In addition to this plasmid, two other plasmids encoding proteins that serve as controls are prepared: full-length HDM-2 without the CAAX sequence, called pHDM2 and HDM-2-CVVK, that lacks amino acid residues 1-109 that constitute the binding site for p53 and for SLH-1, called pdell-109-HDM2-CVVK. All plasmids are prepared at Origene. The following primers are employed to construct the DNA sequences encoding each of the HDM-2 proteins. For these sequences all nuclease sites are given in bold; the start (ATG) and stop (TTA) codons are italicized; and the carboxyl terminal codons for the membrane-localization signal sequence, CVVK (CAAX box), are underlined: Full-length HDM-2:

```
                                      (SEQ ID NO: 29)
CTACAGCGATCGCCATGGTGAGGAGCAGGCAAATGTGC (+strand), (SEQ ID NO: 30)
ACGAGACGCGTGGGGAAATAAGTTAGCACAATCATTTG (-strand);

Full-Length HDM-2 with C-terminal CVVK membrane-
attaching CAAX sequence
                                      (SEQ ID NO: 31)
CTACAGCGATCGCCATGGTGAGGAGCAGGCAAATGTGC (+strand)
                                      (SEQ ID NO: 32)
GCGTACGCGTTTACATAATTACACACTTGGGGAAATAAGTTAGCACAA
TCATTTGG (-strand);

HDM-2-CVVK with residues 1-109 deleted
                                      (SEQ ID NO: 33)
CTACAGCGATCGCCATCTACAGGAACTTGGTAGTAGTC (+STRAND)

(SEQ ID NO: 34)
GCGTACGCGTTTACATAATTACACACTTGGGGAAATAAGTTAGCACA
ATCATTTGG (-STRAND)
```

After digestion with the cloning restriction enzyme Sgf-I and Mlu I, the PCR products are cloned into the Origene Precision Shuttle plasmid pCMV6-AN-GFP with an N-terminal fused GFP-tag. Final constructs are sequenced with VP1.5 5' GGACTTTCCAAAATGTCG 3' (SEQ ID NO: 35) and XL39 5' ATTAGGACAAGGCTGGTGGG 3' (SEQ ID NO: 36) primers.

Transfection of HDM-2 Constructs into Untransformed Cells

The plasmids that are constructed as described above are transfected into untransformed MCF-10-2A cells using transfection methods known in the art, for example in Bowne et al. supra. The transfection efficiency is evaluated by analyzing the GFP fluorescence at 480 nm.

Cell Lines

The following cell lines are obtained from the American Type Culture Collection (Manassas, Va.): MIA-PaCa-2 (human pancreatic cancer), MCF-7 (human breast cancer), A2058 (human melanoma), MCF-10-2A (normal human breast epithelial cells). Ag13145 cells (primary human fibroblasts, 46 chromosome, XY) are obtained from the Coriell Institute for Medical Research (Camden, N.J.) and cultured in DMEM supplemented with 10% fetal bovine serum (FBS; Atlanta Biologicals, Atlanta, Ga.). In addition, two cell lines, i.e., BMRPA1, a normal rat pancreatic acinar cell line, and its k-ras-transformed counterpart pancreatic cancer cell line, called TUC-3 (Kanovsky et al. 2001 Proc Natl Acad Sci USA, 98:12438-12443), both of which were grown in cRPMI medium are useful according to the invention.

The human chronic myeloid K562 leukemia cell line, that lacks p53 expression, was obtained from American Type Culture Collection (ATCC, Manasass, Va.). Cell cultures were maintained in RPMI-1640 media (Sigma-Aldrich, St. Louis, Mo.) supplemented with 10% fetal bovine serum (FBS) and 1% penicillin/streptomycin (P/S) [100 U/100 µg/ml] at 5% $CO_2$ in a humidified incubator at 37° C.

Murine leukocytes. Mouse peritoneal macrophages are isolated by a standard procedure (Zhang et al. 2008 *Curr Protoc Immunol Chapter Unit* 14-1 (DOI: 10.1002/0471142735.im1401s83)) from WT C57B16/j and SphK-1 KO mice. To isolate peritoneal macrophages, the mice are injected with 4% thioglycolate medium intraperitoneally, and peritoneal lavage fluid is collected 72 h post-injection. Next, the CD11b+ macrophages in peritoneal lavage are purified by MACS based positive selection method using CD11b+ magnetic micro beads (Miltenyi Biotech, Auburn, Calif.). Peritoneal macrophages per well are cultured in RPMI-1640 medium (Sigma-Aldrich, St. Louis, Mo.) and incubated at 37° C. in 5% $CO_2$.

Expression of the p53 Peptide of SLH-1

For protein analyses, and detection of apoptosis, $2 \times 10^6$ cells (cancer and non-cancerous cells) are seeded into 10 cm diameter tissue culture plates and transfected with DNA: Lipofectamine 2000 proportionally adjusted to the increased area. When the cell density reaches 90-100%, the cells of the experimental and sham-transfected group are detached using trypsin and plated into four new plates in which they are allowed to grow in complete medium. At defined time points cells are released from adherence with 10 mM EDTA in PBS and are lysed in lysing buffer [1% Triton X-100 in 0.05 M Tris-HCl (pH 8.0), 0.15 mM NaCl, 0.02% Na azide, 0.01 mg/ml phenylmethylsulfonylfluoride (PMSF), and 0.001 mg/ml Aprotinin]. Protein equivalents of $10^6$ cells, i.e., about 30 µg/lane, are then subjected to SDS-PAGE using 10% Tris-HCl gels and, in some experiments, 16% Tricine Peptide Gels (Biorad, Hercules, Calif.) to detect SLH-1 and the p53 portion of SLH-1. The separated proteins are then electrophoretically transferred to nitrocellulose membranes followed by immunoblotting with the mAb DO-1 to p53 AA residues 11-25, and with mAb B-2 to GFP (each at 1 µg-2.5 µg/ml blotting buffer), respectively. After washing non-reacted mAbs from the membranes, the membranes are incubated (1 h) with a second enzyme-labeled antibody from the ECL chemiluminescence kit (Amersham, Piscataway, N.J.) to detect the presence of p53 and the p53 peptide of SLH-1. A time course of GFP expression is performed in both cancer and non-cancerous cells to determine when the highest levels of GFP expression occurs. Semi-quantitation of immunoblotting results is performed by measuring luminosity of bands in a single scanned developed x-ray film, using the histogram option of Adobe Photoshop 5.5. Background is ascertained by measuring average luminosity of 5 areas of the film outside the blotting region. Opacity of each band is calculated by the equation, Opacity=255-Luminosity-background.

Incubation of Cells with SLH-1

Duplicate sets of $6 \times 10^6$ cancer cells are incubated with different concentrations of SLH-1, i.e., 5, 10, 20, 40, 80 and 160 μmol/L. Duplicate control experiments are also performed in which $6 \times 10^6$ cancer cells are incubated with the control, PNC-29, present at a concentration of 75 μmol/L. After the cells have been allowed to adhere to the tissue culture dish (TCD) for 24 hours the medium is removed from each TCD, and new medium containing the same concentration of peptide or no peptide is added. Medium from each TCD is removed every 24 h, and fresh medium with its respective peptide at the appropriate concentration is added. Cells are inspected daily for changes in cell growth, morphology, and viability. At the end of each day over a five-day period, duplicate cell counts are performed for each incubation using the trypan blue exclusion method. In addition, cell viability is also determined by a 3-[4,5-dimethyl-thiazol-2-yl]-2,5 diphenyl tetrazolium bromide (MTT) assay according to the manufacturers' instructions (Promega Corporation, Madison, Wis., USA).

Incubation of Peptides with BMRPA1 Cells

These control cells are untransformed rat pancreatic acinar cells. Duplicate 5-day incubations are performed on $6 \times 10^6$ cells in three circumstances: with no peptide, with SLH-1 at 75 μmol/ml, and with PNC-29 at 75 μmol/ml. Cells are assessed for viability and morphology over this time period. At the end of 5 days, cell counts are performed using the trypan blue exclusion method.

Immunocytochemistry for Annexin V-Binding to Phosphatidyl Serine

To determine whether any of the transfected plasmids induce apoptosis, the cells are evaluated to determine whether the cells contain phosphatidyl serine in the inner cell membrane, identified as binding to annexin-V, as a marker for apoptosis. Cells ($5 \times 10^5$) are seeded in 6-well tissue culture plates 24 h prior to transfection in antibiotic-free medium. Cells are then either transfected with empty vector, vector encoding the p53 portion of SLH-1 or a vector encoding the scrambled peptide or are left untreated. At predetermined time-points post-transfection, the cells are released using 0.5.times Trypsin-EDTA, collected and processed as described in the manufacturer's instructions of the Annexin V-Biotin Apoptosis Detection Kit (CalBioChem, La Jolla, Calif.). The stained cells are resuspended in antifade (Molecular Probes, Oreg.), mounted on glass slides under a glass coverslip and evaluated for red (TRITC) and green (GFP) fluorescence using confocal microscopy as described above.

Evaluation of Cells Treated with SLH-1 for Caspase as a Marker for Apoptosis and LDH Release as a Marker for Necrosis Cancer cells from culture plates at 18, 44, 66 and 90 h time points are lysed in situ in cell lysis buffer [1% Triton X-100 in 0.05 M Tris-HCl (pH 8.0), 0.15 mM NaCl, 0.02% Na azide, 0.1 mg/ml phenylmethylsulfonylfluoride (PMSF), and 0.001 mg/ml Aprotinin]. Lysates are subjected to 10% SDS-PAGE followed by electrotransfer to nitrocellulose and immunoblotting with antibodies to GFP and p53 (Santa Cruz Biotechnology, Santa Cruz, Calif.). Antibody-labeled proteins are identified by chemiluminescence using ECL methodology (Amersham). Assays for elevated caspase expression are performed using the Clontech (Palo Alto, Calif.) for caspase (CPP32) activity. As a positive control for the caspase activity assay, replicate samples of cancer cells are incubated with tumor necrosis factor (TNF) (Sigma, St. Louis, Mo.) at a concentration of 10 ng/ml for 24 h. In addition, to detect if significant cell necrosis occurs, the CytoTox96 assay is used (Promega, Madison, Wis.) to measure LDH released into the cell culture medium.

Lactate dehydrogenase (LDH) assay using the LDH Cytotoxicity Assay (Promega, Madison, Wis.); caspase assay for apoptosis [positive control: $2 \times 10^4$ cells treated with staurosporine (Sigma, St Louis, Mo.) (45 μg/ml)]; and MTT cell viability assay are all performed as described in Do et al. 2003 *Oncogene*, 22:1431-1444; Pincus et al. 2007 *Research Advances in Cancer*, ed Mohan R (Global Research Network Publishers, Kerala, India), pp 65-90; and Bowne et al. 2008 *Ann Surg Oncol*, 15:3588-3600). Protein concentrations are determined using the Bradford assay (Pierce, Rockford, Ill.).

Electron Micropscopy of Cancer Cells Treated with SLH-1

Time-lapse electron microscopy (EM) is used to examine the ultrastructural features of cell death. Cancer cells are grown for 24 h on Thermanox cover slips (Lux Scientific), and then treated with 25 μmol of SLH-1 for 1 and 15 min, along with a corresponding control group without peptide. The cells are washed with PBS solution and then fixed with 2.5% gluteraldehyde-PBS. The fixed cultures are rinsed in a 0.1 M phosphate buffer (pH 7.3), post fixed in 2% (0.08 m) osmium tetroxide-PBS (pH 7.3), dehydrated in a graded series of ethanol and propylene oxide and embedded in Epon 812. Sections are cut at 700 ANG., stained with uranyl acetate and lead citrate and examined with a Jeol JEM 1010 Electron Microscope.

Blotting of Cancer Cell Lysates for p53 and Waf$^{p21}$, a Target for Activated p53

Cell lysates are prepared as described above and are subjected to immunoblotting with either DO-1 antibody described above for expression of the p53 peptide, a (Ab-6) monoclonal anti-p53 antibody (Calbiochem) or with polyclonal anti-waf$^{p21}$ antibody (Santa Cruz Biotechnology, Santa Cruz, Calif.) (1:2000 dilution) as described above. As a control, actin is detected using anti-actin polyclonal antibody (Santa Cruz Biotechnology).

Western Blots

Lysates of $2 \times 10^6$ cells are either used directly or employed for preparation of purified plasma membranes. To assure that the final preparations contains plasma membranes, samples are immunoblotted for membrane β-catenin and by transmission electron microscopy. Blotting of both fractions for H(M)DM-2 is performed in a manner similar to that described previously. Anti-HDM-2 polyclonal antibody (Santa Cruz Biotechnology, Santa Cruz, Calif.) is used at a dilution of 1:4,000. Secondary antibody is HRP-conjugated donkey anti-mouse IgG (HRP-anti-M IgG) (Jackson ImmunoResearch, West Grove, Pa.) used at a dilution of 1:1,000 in 0.1% milk in TBS-T. Immun-Star HRP Peroxide Buffer+ Immun-Star HRP Luminol/Enhancer (ratio 1:1) (BioRad) is added to the nitrocellulose membranes.

Alternatively, after 48 h of treatment with peptides, the cells are harvested from culture plates and lysed in cell lysis buffer containing 1% Triton X-100 in 0.05 M Tris-HCL (pH 8.0), 0.15 mM NaCl, 0.02% sodium azide, 0.1 mg/ml phenylmethylsulfonylfluoride (PMSF), and 0.001 mg/ml Aprotinin. Lysates are subjected to 10% SDS-PAGE followed by electrotransfer to PVDF membrane (Invitrogen, Carlsbad, Calif.) and immunoblotting with DO-1 monoclonal anti-p53 (Santa Cruz Biotechnology Inc., Dallas Tex.) [1:2000] and anti-actin (Sigma-Aldrich, St. Louis, Mo.) [1:4000] antibodies. Antibody-labeled proteins are identified by chemiluminescence using Super Signal West Pico Chemiluminescent Substrate (Thermo Scientific Rockford, Ill.). Bradford Dye Reagent (Bio-Rad Laboratories, Hercules, Calif.) is used to determine the protein concentration.

Immunoprecipitation Experiments

To determine if fluorophore-labeled SLH-1 binds to HDM-2 in cancer cells treated with this peptide, double-fluorophore-labeled SLH-1 (50 µg/ml) is incubated with $1\times10^6$ MIA-PaCa-2 cells for 4 hr. The cells are then lysed (Kanovsky et al. supra; Do et al. supra; Pincus et al. supra; and Bowne et al. supra). Anti-HDM-2 polyclonal antibody (Santa Cruz Biotechnology, Santa Cruz, Calif.), and 500 µg protein in lysate samples are subjected to IP with 0.5 µg anti-MDM2 mouse monoclonal antibody (D-7, Santa Cruz Biotechnology), 2 µg biotinylated horse antimouse IgG (Pierce) and 30 µl 50% suspension of UltraLink-immobilized NeutrAvidin Biotin-Binding Protein beads. The samples are then electrophoresed in 12.5% PAAG gel (Bio-Rad). The position of the fluorescent peptide is analyzed in the gel with Kodak Image Station 2000R. The proteins are transferred to a PVDF membrane, immunoblotted with polyclonal anti-MDM2 antibody (Santa Cruz, N-20), and developed with ECL (Pierce).

Colocalization Experiments and Confocal Microscopy

These experiments are performed on any of the cancer cell lines disclosed herein, or any available cancer cell lines. Cells grown on glass cover slips to 50-60% density are treated for up to 15 min at 37° C. in a humidified 5% $CO_2$-95% air incubator chamber with SLH-1 or PNC-29 (control) at 50 µg/ml incubation medium and are then washed and fixed in 3% paraformaldehyde in PBS (pH 7.2) supplemented with 0.01% glutaraldehyde for 1.5 h followed by extensive washing and transfer into PBS for storage until mounting on glass slides for microscopy. Free aldehyde groups are quenched by incubating cells with glycine (0.2 M) and sodium borohydride (75 mM) followed by washing in PBS. Cells are then stained (direct staining) for 2 h, 4° C., with fluorescein-labeled mouse monoclonal antibody against p53 [FITC-mAbα-p53 (DO-1)] (5 µg/ml) and rhodamine-labeled (TRITC-) mAba-against H/R/MDM-2 (5 µg/ml) (both labeled antibodies, Pierce) in 1% FBS-PBS. After removal of nonreactive Ab and extensive washing, the cover slips are mounted on glass slides over Prolong Gold Antifade (Molecular Probes, Invitrogen, Carlsbad, Calif.) and examined with a laser-equipped Olympus Confocal microscope 1×76 (Olympus America Inc, Center Valley, Pa.). Results are digitally recorded. The colocalization of the two antibodies is confirmed by overlapping green (anti-SLH-1) and red (antiH/R/MDM-2) fluorescent labels that produce yellow fluorescence (combined green and red fluorescence).

Dose Response Experiments

LDH assays are performed on different cancer cell lines (n=3-5) that are incubated for 30 min with SLH-1 over a concentration range of 10 µg·ml-1 mg/ml as described previously (Do et al. supra; Pincus et al. supra; and Bowne et al. supra).

Treatment of Transfected Cells with SLH-1

Transfected cells in media are incubated at 37° C. with 5% $CO_2$ for 24 h, at which time they are treated with SLH-1 peptide (sonicated briefly prior to addition) such that the final concentration is 300 µg/ml. Samples are assayed for LDH, MTT, and caspase. In addition, samples are processed for confocal microscopy as described above except for the following modification. Because the cells contain GFP, to localize SLH-1, it is necessary to use another fluorescent probe other than green-fluorescent FITC-labeled DO1 antibody. Cells are incubated with unlabeled DO1 and anti-HDM-2 as described above. The cells are then washed and incubated with Alexa Fluor 647 goat antimouse IgG (1:200) (against DO1 mouse) (Invitrogen-Molecular Probe, Eugene, Oreg.) and TAMRA-labeled goat antirabbit IgG (1:200) (against anti-HDM-2 rabbit polyclonal IgG) (Sigma, St. Louis, Mo.). The cells are processed for confocal microscopy, and the membrane fractions and whole cell lysates are blotted for either HDM-2 or actin [rabbit anti-actin-42 polyclonal antibody (1:5000)] (Sigma).

Alternatively, after reaching the desired confluence cells are incubated with different concentrations of SLH-1 or PNC-29 (i.e., 25, 50, 75, 100 µM) in tissue culture dishes (TCD) for 24 h. For 48 h treatments, the same peptide concentration is added on the second day as described previously (Karnovsky et al. supra). Cells are inspected daily for changes in cell growth, morphology, and viability. At the end of a 48 h period, cell viability is determined by MTT (3-[4,5-dimethylthiazol-2yl]-2,5-diphenyl tetrazolium bromide) assay according to the manufacturer's instruction (Promega, Madison, Wis.)

Confocal Microscopy

Cells ($2\times10^6$) are maintained in RPMI-1640 Media (Sigma-Aldrich, St. Louis, Mo.) supplemented with 10% FBS and 1% P/S [100 U/100 µg/ml] and are treated with SLH-1 (100 µg/ml) or PNC-29 (100 µg/ml) for 1 h in 5% $CO_2$ humidified incubator at 37° C. All samples are then washed repeatedly with PBS. The cells are fixed with 4% formaldehyde in PBS for 5 minutes at room temperature and blocked with PBS containing 5% bovine serum albumin (BSA) and 0.3% Triton x-100 for 1 h on a shaker at room temperature. An antibody mixture of DO1 anti-p53 [1:250] (Santa Cruz Biotechnology Inc., Dallas Tex.) that recognizes p53 aa 11-25 that overlaps the modified 12-26 p53 sequence of SLH-1 and anti-HDM-2 polyclonal antibody (N-20, sc813, Santa Cruz Biotechnology, Dallas, Tex.) [1:250] in 1% BSA and 0.3% Triton x-100 containing PBS is added to cells overnight on a rotator at 4° C. The cells are then washed extensively with PBS and treated with a mixture of secondary antibodies, the polyclonal goat to mouse green-fluorophore (DyLight® 488) [1:200] (Abcam Inc., Cambridge, Mass.) and polyclonal goat to rabbit red fluorophore (DyLight® 650) [1:200] (Abcam Inc., Cambridge, Mass.) in PBS containing 1% BSA and 0.3% Triton x-100 overnight on a rotator at 4° C. After incubation cells are washed repeatedly with PBS and visualized on glass slides under the Olympus Fluoview FV1000 confocal microscope (Olympus America INC, Center Valley, Pa.) using a 60× NA 1.42 PLAPON oil objective. Sequential image recording has been applied to avoid spectral overlap. Image analysis is performed using Olympus FV10-ASW 1.7 Viewer software.

Compositions useful according to the invention include SLH-1 in combination with additional peptides and/or non-peptide materials which may desirably have an HDM-2 affinity or binding site and may be used in conjunction with the MRP. Hybrid materials containing peptide and non-peptide components, along with wholly non-peptide materials may be used with one or more of the methods of the present invention. The synthesis of one or more of the compounds may be subsequently followed by purification, as is commonly done in the art. The compounds synthesized are preferably in purified form to be used as the compound and with the methods of the present invention. Thus, the present invention contemplates the use of peptide as well as non-peptide materials, and combinations thereof, to cause selective necrosis to cancer cells, in accordance with the present invention.

It should be readily understood and appreciated that each of the elements and features of the present invention discussed with one embodiment may be similarly employed with other embodiments disclosed herein, and this discussion is by no means deemed limiting to the various additional permutations that may be employed, for example, with the methods presented herein.

Unless defined otherwise, all technical and scientific terms used herein have the meaning commonly understood by a person skilled in the art to which this invention belongs. The following references provide one of skill with a general definition of many of the terms used in this invention: Singleton et al., Dictionary of Microbiology and Molecular Biology (2nd ed. 1994); The Cambridge Dictionary of Science and Technology (Walker ed., 1988); The Glossary of Genetics, 5th Ed., R. Rieger et al. (eds.), Springer Verlag (1991); and Hale & Marham, The Harper Collins Dictionary of Biology (1991). As used herein, the following terms have the meanings ascribed to them below, unless specified otherwise.

The present invention is described by reference to the following Examples, which are offered by way of illustration and are not intended to limit the invention in any manner Standard techniques well known in the art or the techniques specifically described below are utilized.

EXAMPLES

Example 1

Cytotoxicity of SLH-1 for Cancer Cells

SLH-1 is incubated with $6 \times 10^6$ cancer cells, for example, Mia-PaCa-2 cells, for 5 days at concentrations ranging from 12.5-75 μmol/ml. At different timepoints following treatment the cells are assessed for signs of necrosis, for example, membrane blebbing and disruption and formation of cell clumps coalescing into aggregates of cellular debris. Percent cell death is determined by measuring trypan blue dye uptake. Cancer cells are also treated with the negative control peptide PNC-29 and, separately, a peptide having only the p53 derived portion of SLH-1 that cannot traverse the cell membrane due to the lack of the MRP peptide, administered at the same concentration as the test peptide. The effect of these control peptides on cellular growth, morphology and viability is determined.

As an additional control, SLH-1 is combined with untransformed BMRPA1 acinar cells and with the untransformed breast epithelial cell line, MCF-10-2A at a concentration ranging from 12.5-75 μmol/ml to determine if the peptide is lethal to normal cell growth.

Example 2

Markers for Necrosis and Apoptosis in Cancer Cells Treated with SLH-1

Cell death can occur by either necrosis or apoptosis. p53-targeting treatments typically cause cell death through apoptosis. Necrosis is not genetically controlled, while apoptosis is genetically controlled. Apoptosis is the deliberate cellular response to specific environmental and developmental stimuli or programmed cell death. Cells undergoing apoptosis exhibit cell shrinkage, membrane blebbing, chromatin condensation and fragmentation. Necrosis involves the destruction of cytoplasmic organelles and a loss of plasma membrane integrity. Though apoptosis does not have the inflammation which results when cancer cells die through necrosis, p53 targeting treatments fail to treat those cancers that do not exhibit p53, or, through mutations, exhibit an inactive p53 form that is unresponsive to p53 targeted treatments. After the DNA damage in the caspase enzyme pathway, there are a series of events which occur that involve calcium activation and calpain enzymes which further leads to other cellular changes and regulation of cytoplasmic enzymes. During p53-dependent apoptosis, there is a sequential expression of annexin V-binding membrane phospho-Serine, Bax waf$^{p21}$, and caspases; these proteins are used as markers for p53-dependent apoptosis.

A major difference between necrosis and apoptosis in vivo is the complete elimination of the apoptotic cell before an inflammatory response is seen. Necrosis usually causes inflammation. Though apoptosis can be thought of as a clean and neat process, the p53 targeting treatments do not result in apoptosis in all types of cancer cases. Though necrosis may typically cause an inflammatory response to a treatment site directed at targeting HDM-2, HDM-2-targeting treatments are more effective against various forms of cancer, including those where p53 is not present in the cancer cells, or where p53 is in a mutated or an inactive form.

To determine if SLH-1 induces cell death by necrosis or by apoptosis, the expression of LDH and caspase in cancer cells treated with SLH-1 is determined as described above. Early release of LDH (elevation of LDH levels) indicates necrosis Elevated levels of caspase are indicative of apoptosis Electron micrographs of cancer cells or non-cancerous cells treated with SLH-1 and untreated cells are performed to determine if the cells exhibit lysis of their plasma membranes or have intact plasma membranes. Lysis of plasma membranes is characteristic of tumor cell necrosis.

Example 3

Transfection of Cancer Cells with a Plasmid that Encodes the p53 Sequence of SLH-1

Cancer cells and non-cancerous cells are transfected with empty vector or a green fluorescent protein encoding vector encoding the p53 sequence of SLH-1. After 2 hours post-transfection, cell counts are performed on slides using light microscopy followed by counting the number of cells exhibiting green fluorescence from GFP (Green Fluorescent Protein). Morphological examination of transfected cells, as visualized by inverted light microscopy is also performed to identify cells that are nephrotic or apoptotic.

Cancer cells, for example MiaPaCa-2 cells expressing GFP that are transfected with empty vector a vector expressing the p53 sequence of SLH-1 are lysed and blotted for p53, waf$^{p21}$, a protein that is induced by a p53-dependent pathway, and the p53 17-26 peptide itself. In these experiments, the DO-1 anti-p53 antibody that recognizes a determinant that contains residues 17-26 of p53 is used. In addition, caspase activity in these cells is measured. For comparison, the same set of experiments are performed on cancer cells treated with 75 μmol/ml of SLH-1. Caspase activity and p53$^{waf21}$ levels are determined. For controls, actin is blotted for.

In the early stages of apoptosis, phosphatidyl serine (PS), normally present in the inner leaflet of the bilayer membrane of intact cells, is found on the external plasma membrane of cells undergoing apoptosis. Annexin V binds PS and can be located by a probe that carries the red fluorescent TRITC probe. Cells that are transfected with the p53 sequence of SLH-1 or control vector are processed for staining with Annexin V-biotin followed by streptavidin-TRITC and examined by confocal microscopy. Control experiments with BMRPA1 control cells transfected with a vector expressing the p53 sequence of SLH-1 or a control vector are also performed and these cells are analyzed for expression of Annexin V.

Example 4

Transfection of Cells with pTracer-SV40 Plasmid Encoding Only the p53 Sequence of SLH-1

To define the role of the MRP definitively, the effects of the p53 peptide of SLH-1 itself on tumor cell growth, i.e., whether even without the MRP, it could induce tumor cell necrosis, are determined. The p53 peptide of SLH-1 is introduced into cancer cells via transfection using the pTracer-SV40 plasmid that constitutively expresses this peptide. The expression of markers for apoptosis and necrosis in the transfected cells are measured and compared with the levels of these markers in replicate samples of cancer cells treated with SLH-1. These experiments are also performed in BMRPA1 control cells.

Example 5

Induction of Apoptosis in Cancer Cells Treated with the p53 Peptide of SLH-1

Experiments are performed in cancer cells expressing the p53 peptide of SLH-1. To determine if apoptosis is occurring, the expression of $Waf^{p21}$ is determined. Apoptosis is indicated by increased levels of $Waf^{p21}$. The level of caspase is also determined. An increase in the level of caspase is indicative of apoptosis. The level of expression of annexin-V-binding phosphatidyl serine in the membranes, a known early phenomenon in apoptosis, is determined in cancer cells transfected with the p53 peptide of SLH-1 as well as cells transfected with empty vector. The level of LDH release is also measured. It is expected that an increase in the release of LDH will occur if the peptide induces tumor cell necrosis.

Example 6

In Vivo Analysis of SLH-1 Activity

Nu/Nu mice (Harlan Laboratories, Indianapolis, Ind., n=10) weighing 20-22 g, are xenotransplanted subcutaneously (s.c.) with live pancreatic carcinoma cells BMRPA1.TUC-3 ($1\times10^6$ cells/mouse) in the left hind region. Tumors are allowed to develop and grow.

After tumor formation has occurred, the mice are separated into three groups. Each group is implanted s.c. with Alzet™ osmotic pumps to deliver in a constant rate and over a defined period of 14 days a total volume of 0.095 ml volume of normal saline containing the peptide at a concentration of 20 mg/mouse. One group of mice receives SLH-1 (SEQ ID NO:2) fused at its carboxy terminal end to the penetratin leader sequence (SEQ ID NO:3) and the other group of mice receives PNC-29, a control peptide of similar size, having the following amino acid sequence: MPFSTGKRIMLGE (SEQ ID NO: 37). A third group of mice does not receive peptide. The pumps are filled according to the manufacturers guidelines and under sterile conditions The pumps are implanted s.c. on the left flank of the anaesthetized mice by creating a pocket underneath the mouse skin into which the tiny pumps are inserted. Each pocket is closed with a simple suture. From their inside chamber the pumps deliver continuously 0.25 µl/hr into each mouse. The mice are observed until they have recovered from the surgery and are then returned to the isolation ward of the animal facility. Since the animals are Nu/Nu mice and, thus, immuno-compromised they are highly susceptible when exposed to pathogens. Surgery and all preceding and post-surgical treatments are therefore performed in a sterile hood Alternatively, using the same methodology as described above, live pancreatic carcinoma cells BMRPA1.TUC-3 ($1\times10^6$ cells/mouse) are transplanted to the peritoneal cavity of five mice and pumps are placed in the right shoulder region at the same time of tumor cell transplantation.

All patents and publications mentioned in the specification are indicative of the levels of skill of those skilled in the art to which the invention pertains. All references cited in this disclosure are incorporated by reference.

One skilled in the art would readily appreciate that the present invention is well adapted to carry out the objects and obtain the ends and advantages mentioned, as well as those inherent therein. The methods and compositions described herein as presently representative of preferred embodiments are exemplary and are not intended as limitations on the scope of the invention. Changes therein and other uses will occur to those skilled in the art, which are encompassed within the spirit of the invention, are defined by the scope of the claims.

It will be readily apparent to one skilled in the art that varying substitutions and modifications can be made to the invention disclosed herein without departing from the scope and spirit of the invention. Thus, such additional embodiments are within the scope of the present invention and the following claims.

The invention illustratively described herein suitably can be practiced in the absence of any element or elements, limitation or limitations that are not specifically disclosed herein. Thus, for example, in each instance herein any of the terms "comprising", "consisting essentially of", and "consisting" of may be replaced with either of the other two terms. The terms and expressions which have been employed are used as terms of description and not of limitation, and there is no intention that in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments, optional features, modification and variation of the concepts herein disclosed may be resorted to by those skilled in the art, and that such modifications and variations are considered to be within the scope of this invention as defined by the description and the appended claims.

In addition, where features or aspects of the invention are described in terms of Markush groups or other grouping of alternatives, those skilled in the art will recognize that the invention is also thereby described in terms of any individual member or subgroup of members of the Markush group or other group.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Embodiments of this invention are described herein, including the best mode known to the inventors for carrying out the invention. Variations of those embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

What is claimed is:

1. A peptide comprising the amino acid sequence PPLSQTSFAEYWNLLSP (SEQ ID NO: 2).

2. A peptide comprising the amino acid sequence: H-Pro-Pro-Leu-Ser-Gln-Thr-Ser-Phe-Ala-Glu-Tyr-Trp-Asn-Leu-Leu-Ser-Pro-Lys-Lys-Trp-Lys-Met-Arg-Arg-Asn-Gln-Phe-Trp-Val-Lys-Val-Gln-Arg-Gly-OH (SEQ ID NO: 3).

3. The peptide of claim 1, further comprising a membrane penetrating amino acid sequence.

4. The peptide of claim 3, wherein said membrane penetrating sequence forms the carboxy terminal sequence of said peptide.

5. The peptide of claim 3 or 4, wherein said membrane penetrating sequence comprises the amino acid sequence: KKWKMRRNQFWVKVQRG (SEQ ID NO: 4).

6. The peptide of claim 3, wherein the peptide has increased cellular uptake as compared to the peptide of claim 1.

7. A peptide having a length of 17 amino acids to 35 amino acids, comprising a sequence consisting of the amino acid sequence PPLSTSFAEYWNLLSP (SEQ ID NO: 2).

8. A composition comprising the peptide of claim 1 or 2.

9. A pharmaceutical composition comprising the peptide of claim 1 or 2, in combination with a pharmaceutically acceptable carrier.

10. A kit comprising the peptide of claim 1 or 2 and instructions for use.

11. A method of treating cancer in a subject in need thereof, comprising administering to the subject a therapeutically effective amount of a composition comprising the peptide of claim 1 or 2, wherein the cancer is selected from the group consisting of: astrocytoma, bladder cancer, brain cancer, breast cancer, cervical cancer, colorectal cancer, endometrial cancer, gastric cancer, lung cancer, melanoma, leukemia, lymphoma, ovarian cancer, pancreatic cancer, prostate cancer, renal carcinoma, sarcoma, thyroid cancer, glioblastoma, multiple myeloma, myelodysplastic syndrome, mesothelioma, acute myeloid leukemia, childhood leukemia, chronic myeloid leukemia, myelodysplastic syndrome, Hodgkin's lymphoma, and Polycythemia Vera.

12. A method of selectively necrosing cells, comprising providing a plurality of cells, comprising at least one cancer cell and at least one normal cell, administering to the cells a composition wherein the composition comprises the peptide of claim 1 or 2, and wherein said composition results in membranolysis of said cancer cells, but does not affect said normal cells.

13. A method of causing membranolysis in cancer cells, comprising administering to at least one cancer cell a composition comprising the peptide of claim 1 or 2.

* * * * *